United States Patent
Andrianov et al.

(10) Patent No.: US 7,217,781 B2
(45) Date of Patent: May 15, 2007

(54) POLYPHOSPHAZENES INCLUDING IONIC OR IONIZABLE MOIETIES AND FLUORINE-CONTAINING MOIETIES

(75) Inventors: Alexander K. Andrianov, Belmont, MA (US); Alexander Marin, Newton, MA (US)

(73) Assignee: Parallel Solutions, Inc., Cambridge, MA (US)

( * ) Notice: Subject to any disclaimer, the term of this patent is extended or adjusted under 35 U.S.C. 154(b) by 35 days.

(21) Appl. No.: 11/103,251

(22) Filed: Apr. 11, 2005

(65) Prior Publication Data

US 2005/0234210 A1 Oct. 20, 2005

(51) Int. Cl.
*C08G 79/02* (2006.01)
(52) U.S. Cl. ............... 528/398; 528/399; 528/401; 528/486; 528/488; 424/280.1
(58) Field of Classification Search ............... 528/398, 528/399, 401, 486, 488; 424/280.1
See application file for complete search history.

(56) References Cited

OTHER PUBLICATIONS

Drappel et al., Conductive coated carriers comprised of inorganic and organic polymers mixture for electrophotographic developer, Xerox corporation, Jul. 2002, Chem Abstract 137: 116908.*
Drapper et al., Conductive coated carriers comprised of inorganic and organic polymers mixture for electrophotographic developer, Xerox corporation, Jul. 2002, Chem Abstract 137: 116907.*
Denness et al., Synthesis of crown ether polymers—lithium doped materials, Physical organic Chemistry, 1994, (7), 1445-53, Chem Abstract 121: 109821.*
Nakanaga et al., Fluoroalkylsulfonyl gorup containing oligoalkyleneoxypolyphosphazenes and their uses, Otsuka Chemical Co., LtD., Japan, 1990, Chem Abstract 113: 232301.*

* cited by examiner

*Primary Examiner*—Duc Truong
(74) *Attorney, Agent, or Firm*—Elliot M. Olstein; Raymond J. Lillie

(57) ABSTRACT

A polyphosphate polymer which includes both (i) ionic or ionizable moieties; and (ii) fluorine-containing moieties. Such polymers may be used as matrices for pharmaceuticals, as multilayer coatings for fuel cell membranes, as dopant for electrically conductive polymers, or as multilayer coatings for biomedical devices.

19 Claims, No Drawings

POLYPHOSPHAZENES INCLUDING IONIC OR IONIZABLE MOIETIES AND FLUORINE-CONTAINING MOIETIES

This invention relates to polyphosphate polymers. More particularly, this invention relates to polyphosphazene polyelectrolyte polymers which include ionic or ionizable moieties and fluorine-containing moieties.

Polyphosphazenes are polymers with backbones consisting of alternating phosphorus and nitrogen atoms, separated by alternating single and double bonds. Each phosphorus atom is bonded covalently to two pendent groups (R). Thus, polyphosphazenes in general have the following structural formula:

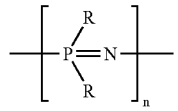

wherein n is an integer.

Each phosphorus atom in the polyphosphate polymer can be bound to two identical pendent "R" groups. In general, when the polyphosphate has more than one type of pendent group, the groups will vary randomly throughout the polymer, and the polyphosphazene thus is a random copolymer. A polyphosphazene with two or more types of pendent groups may be produced by reacting poly (dichlorophosphazene) with the desired nucleophile or nucleophiles in a desired ratio. The ratio of pendent groups in the polyphosphazene is determined by a number of factors, including the ratio of starting materials used to produce the polymer, the temperature at which the nucleophilic substitution reaction is carried out, and the solvent system used.

In accordance with an aspect of the present invention, there is provided a polyphosphazene polymer having the formula:

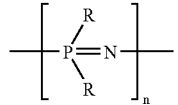

In each monomeric unit of the polyphosphazene polymer, each R is the same or different. At least a portion of the R groups are $R_1$ groups, wherein $R_1$ contains an ionic or ionizable moiety, and at least a portion of the R groups are $R_2$ groups, wherein $R_2$ contains a fluorine-containing moiety.

$R_1$ has the formula:

$Y_1$-$X_1$-$Z_1$ $Y_1$ is oxygen, nitrogen, or sulfur. $X_1$ is selected from the group consisting of alkyl, aryl, aralkyl, allyl, alkoxy, aryloxy, alkylaryloxy, alkylamino, arylamino, and alkylarylamino. $Z_1$ is an ionic or ionizable moiety.

$R_2$ has the formula:

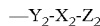
—$Y_2$-$X_2$-$Z_2$ $Y_2$ is oxygen, nitrogen, or sulfur. $X_2$, is selected from the group consisting of alkyl, aryl, aralkyl, alkylaryl, allyl, alkoxy, aryloxy, alkylaryloxy, alkylamino, arylamino, and alkylarylamino. $Z_2$ is a fluorine-containing moiety. n is from about 10 to about 300,000. The polymer includes both $R_1$ and $R_2$ groups.

In one embodiment, n is from about 5,000 to about 20,000.

In another embodiment, each of $Y_1$ and $Y_2$ is oxygen.

In a further embodiment, the ratio of $R_1$ to $R_2$ in the polyphosphazene polymer is from 1:99 to 99:1, preferably from 1:50 to 1:2.

The ionic or ionizable moiety $Z_1$ may be an anionic moiety or a cationic moiety. Anionic moieties which may be included in the polyphosphazene polymer include, but are not limited to carboxylic acid moieties, sulfonic acid moieties, phosphonic acid moieties, and salts thereof.

Particularly preferred $R_1$ groups which include anionic moieties are as follows:

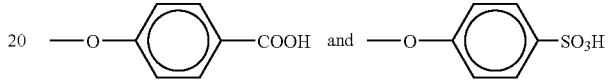

In another embodiment, $Z_1$ is a cationic moiety. Cationic moieties which may be included in the polyphosphazene polymer include but are not limited to, amino moieties, and ammonium salts. The resulting $R_1$ group thus may include primary, secondary, tertiary, and quaternary amines, and may include primary, secondary, teritary, and quaternary ammonium salts. A particularly preferred $R_1$ group including a cationic moiety is —$OCH_2CH_2CH_2NH_2$.

In another embodiment, the fluorine-containing moiety $Z_2$ is $CF_3$ or $CF_2H$. Particularly preferred $R_2$ groups which include the flourine-containing moiety are —$OCH_2$ $CF_3$, —$OCH_2$ $CH_2$ $CF_3$, —$OCH_2$ $(CF_2)_a$ $CF_3$, wherein a is from 1 to about 1,000, —$OCH_2$ $(CF_2)_a$ $CF_2H$, wherein a is from 1 to about 1,000, and —$OC_6H_4CF_3$.

In one embodiment, $Y_1$ is oxygen, $X_1$ is phenyl, $Z_1$ is a carboxylic acid moiety, $Y_2$ is oxygen, $X_2$ is —$CH_2$, -$Z_2$ is $CF_3$, and the polyphosphazene polymer has the following structure:

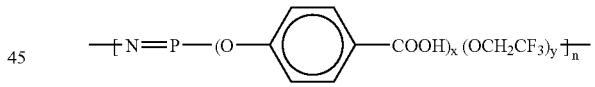

wherein n is as hereinabove described, and x plus y is 2.

In yet another embodiment, $Y_1$ is oxygen, $X_1$ is phenyl, $Z_1$ is sulfonic acid, $Y_2$ is oxygen, $X_2$ is —$CH_2$-, $Z_2$ is $CF_3$, and the polyphosphazene polymer has the following structural formula:

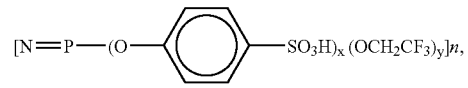

wherein n is as hereinabove described, and in each monomeric unit, x plus y is 2.

In yet another embodiment, $Y_1$ is oxygen, $X_1$ is propyl, $Z_1$ is $NH_2$, $Y_2$ is oxygen, $X_2$ is —$CH_2$—, and $Z_2$ is $CF_3$, and the polyphosphazene polymer has the following structural formula: [N=P—($OCH_2$ $CH_2$ $CH_2$ $NH_2$)$_x$(—$OCH_2CF_2$)$_y$]$_n$, wherein n is as hereinabove described, and in each monomeric unit, x plus y is 2.

In a further embodiment, at least a portion of the R groups are side groups $R_3$. $R_3$ side groups include, but are not limited to, side groups suitable for cross-linking, side groups to improve mechanical properties, biodegradable side groups, and side groups that improve water solubility and hydrophilicity of said polymer. Examples of side groups suitable for cross-linking include, but are not limited to, eugenoxy groups, allyloxy groups, alkylphenoxy groups, chlorophenoxy groups, allylamino groups, and chlorine. Examples of side groups to improve mechanical properties include, but are not limited to, alkylphenoxy and phenylphenoxy groups. Suitable biodegradable side groups include, but are not limited to, chlorine, amino acids, amino acid esters, and imidazolyl, glycinyl, glyceryl, glucosyl, and ethoxy groups. Examples of side groups that improve water solubility and hydrophilicity include, but are not limited to, alkylether side groups.

In yet another embodiment, at least a portion of the R groups are targeting side groups $R_4$. Targeting side groups which may be employed include, but are not limited to, antibodies, lectins, tri-and tetraantennary glycosides, transferrin, and other molecules which are bound specifically by receptors on the surfaces of cells of a particular type.

The polyphosphazenes of the present invention may be prepared by a macromolecular nucleophilic substitution reaction of a polyphosphazene substrate, such as poly(dichlorophosphazene), with a wide range of chemical reagents or mixture of reagents in accordance with methods known to those skilled in the art. Preferably, the polyphosphazenes of the present invention are made by reacting poly(dichlorophosphazene) with an appropriate nucleophile or nucleophiles that displace chlorine. Desired proportions of the $R_1$ and $R_2$ groups, and $R_3$ and $R_4$ groups if needed, can be obtained by adjusting the quantities of the corresponding nucleophiles that are reacted with poly (dichlorophosphazene) and the reaction conditions as necessary.

Alternatively, the polyphosphazene substrate is a polydichlorophosphazene derivative wherein some of the chlorine atoms have been replaced with organic side groups. Thus, the substrate is a copolymer of polydichlorophosphazene and polyorganophosphazene.

The nucleophilic substitution reaction of the polyphosphazene substrate with the desired proportions of the $R_1$ and $R_2$ groups, and $R_3$ and $R_4$ groups if needed, takes place in an appropriate organic solvent. Organic solvents in which the reaction is effected include, but are not limited to, diglyme, chlorobenzene, dichlorobenzene, dichloroethane, N,N-dimethylformamide (DMF), N,N-dimethylacetamide, dioxane, tetrahydrofuran (THF), toluene, methylsulfoxide, and dimethylsulfone, and mixtures thereof. The reaction mixture then is subjected to appropriate reaction conditions, including heating, cooling, and/or agitation. The reaction mixture then may be filtered, if necessary, and organic and aqueous layers then are separated. Depending on the polymer structure, the polymer is isolated from the aqueous or organic phase by precipitation. The resultant polymer then is dried. The organic solvent and reaction conditions employed are dependent upon a variety of factors, including, but not limited to, the polyphosphazene substrate employed, the $R_1$ and $R_2$ groups, and $R_3$ and $R_4$ groups if included, and the proportions thereof.

Preferably, the polyphosphazene polymers of the present invention have a molecular weight of at least 1,000 g/mole, more preferably from about 500,000 g/mole to about 1,500,000 g/mole.

In one embodiment, the $R_1$ and $R_2$ groups, and $R_3$ and $R_4$ groups if employed, are distributed randomly throughout the polyphosphazene polymer.

Thus, with the proviso that the polymer includes both $R_1$ and $R_2$ groups, each monomeric unit of the polymer may be any one of the following:

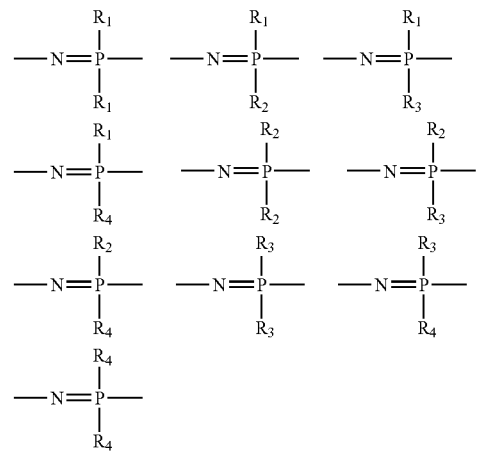

These monomeric units may be distributed randomly or in blocks throughout the polymer, provided that the polyphosphazene polymer includes both $R_1$ and $R_2$ groups.

Furthermore, in accordance with the present invention, the polyphosphazene polymer may include more than one specific $R_1$ group, and/or may include more than one specific $R_2$ group, and/or may include more than one specific $R_3$ group and/or may include more than one specific $R_4$ group.

The polyphosphazene polymers of the present invention may be used as proton conductive materials, dopant for electrically conductive polymers, modifiers of surface properties, especially coating agents to produce mono-and multilayer films, and cross-linkable materials, including biomedical implants and articles of controlled release for biologically active agents.

The polyphosphazene polymers of the present invention may be used as proton conductive materials in fuel cells. Fuel cells are electrochemical cells in which a free energy change resulting from a fuel oxidation reaction is converted into electrical energy. The process is accomplished utilizing a proton exchange membrane (PEM) sandwiched between two electrodes, namely an anode and a cathode. Polyphosphazenes of the present invention can be used as membrane materials to increase conductivity, to minimize fuel crossover, and to improve operating temperature range in fuel cells.

The polyphosphazene polymers of the present invention may be used as dopant for electrically conductive polymers. Electrically conductive polymers have a conductivity which can be modified with electron acceptor or donor dopant to be greater than the conductivity of the unmodified polymer. Polyacetylene and polyaniline are examples of organic polymers whose electrical conductivity at room temperature is modified over several orders of magnitude above its insulator state by the incorporation of dopant (U.S. Pat. No. 4,222,093). Other examples of organic polymeric materials whose room temperature electrical conductivity can be enhanced by several orders of magnitude over their insulator state by means of incorporation of dopant molecules are poly-p-phenylene, polypyrrole, poly-1,6 heptadiyne, and polyphenylene vinylene. (U.S. Pat. No. 4,579,679)

The dopant modified electroactive polymer has a charge opposite to the conductivity modifier, i.e., the ionic dopant. Dopant can render the polymer electrically conductive as well as to provide improved solubility to conductive polymers.

The polyphosphazene polymers of the present invention may be used as coating agents for the construction of monolayer and multilayer assemblies. Such assemblies are constructed by layer-by-layer polyelectrolyte deposition. This includes direct adsorption of polyelectrolytes onto suitable solids, at the interface between the solid and a fluid phase containing the monolayer forming molecules. The process can be continued until the targeted number of monolayers, one upon the other, is obtained (U.S. Pat. No. 4,539,061). Typically, a multilayer coating can contain 5 to 20 layers of polyelectrolytic materials. Desired functional groups can be included at the upper surface of the coating to obtain a surface with a required set of properties. Multilayer coatings can be used in a wide range of industrial applications, such as but not limited to, preparation of artificial membranes, fabrication of passive and active ultrathin film components for novel microelectronic and optical devices, ultrathin photoresists, and molecular films useful in solar energy conversion, etc. Multilayer coatings can be used in biomedical devices. Biomedical devices include a wide variety of devices used in the biological, medical, or personal care industries and include, but are not limited to, ophthalmic lenses, drug delivery devices such as oral osmotic devices and transdermal devices, catheters, contact lens disinfection and cleaning containers, breast implants, stents, intervertebral discs, artificial organs and tissues, and the like.

Many devices and materials used in biomedical applications require certain properties in the bulk of the device or material with distinct and separate properties required for the surface. For example, a contact lens may have a core or bulk material which is highly oxygen permeable and hydrophobic, and a surface which has been treated or coated to increase the hydrophilicity, thereby allowing the lens to move freely on the eye. Other biomaterials require coatings effective in preventing protein adsorption on biosurfaces and preventing fouling.

In addition, the polyphosphazene polymers of the present invention may be used as bioelastic in situ cross-linkable materials for injectable implants in plastic or reconstructive surgery. Such injectable compositions of the invention are useful in plastic surgery, for example, for tissue reconstruction or dermal augmentation (for example, filling in dermal creases and providing support for skin surfaces), sphincter augmentation (for example, for restoration or urinary continence), tumor blood vessel blockage, tumor therapy, and infertility treatments. (U.S. Pat. No. 6,699,294). Another area for use of injectable implants and bioelastic materials is the restoration or repair of an injured intervertebral disc. In order to restore an intervertebral disc in a mammal, the polymer is injected into the depleted nucleus pulposus site in an aqueous solution, and then the polymer cross-links and swells to increase the pressure within the disc. The polymers can be prepared with different water-containing compositions, with a wide range of hydrophobicities, with almost any desired elastic modulus, and with a variable degree of cross-linking by selecting side groups for and by varying the cross-linking process (e.g., chemical, enzymatic, or radiation) used to form the final product. The cross-linking can be achieved for example, in the presence of multivalent ions, such as calcium, spermine, spermidine, etc.

In addition, the polyphosphazene polymers of the present invention may be used in controlled release formulations and can be dissolved and/or suspended in water or any other suitable liquid medium in which the polymers are soluble and/or dispersible and combined with a pharmacological or pharmaceutical compound or composition to form a composition of matter. The polymer will act as a matrix for the pharmaceutical to provide an article of manufacture for the controlled release of such pharmaceutical.

Alternatively, the polymers may be used for the encapsulation of pharmaceutical agents to produce microspheres, microcapsules, micelles, or the polymers may be used to stabilize liposomes.

Pharmaceuticals which may be included in the resulting article of manufacture are listed in the *Physicians' Desk Reference*, 57th Edition (2003), and include allergens, amebicides and trichomonacides, amino acid preparations, analeptic agents, analgesics, analgesics/antacids, anesthetics, anorexics, antacids, antihelmintics, antialcohol preparations, antiarthritics, antiasthma agents, antibacterials and antiseptics, antibiotics, antiviral antibiotics, anticancer preparations, anticholinergic drug inhibitors, anticoagulants, anticonvulsants, antidepressants, antidiabetic agents, antidiarrheals, antidiuretics, antienuresis agents, antifibrinolytic agents, antifibrotics (systemic), antiflatulents, antifingal agents, antigonadotropin, antihistamines, antihyperammonia agents, anti-inflammatory agents, antimalarials, antimetabolites, anti-migraine preparations, antinauseants, antineoplastics, anti-obesity preparations, antiparasitics, anti-parkinsonism drugs, antipruritics, antipyretics, antispasmodics and antichloinergics, antitoxoplasmosis agents, antitussives, antivertigo agents, antiviral agents, biologicals, bismuth preparations, bone metabolism regulators, bowel evacuants, bronchial dilators, calcium preparations, cardiovascular preparations, central nervous system stimulants, cerumenolytics, chelating agents, choleretics, cholesterol reducers and anti-hyperlipemics, colonic content acidifiers, cough and cold preparations, decongestants, expectorants and combinations, diuretics, emetics, enzymes and digestants, fertility agents, fluorine preparations, galactokinetic agents, geriatrics, germicides, hematinics, hemorrhoidal preparations, histamine H. receptor antagonists, hormones, hydrocholeretics, hyperglycemic agents, hypnotics, immunosuppressives, laxatives, mucolytics, muscle relaxants, narcotic antagonists, narcotic detoxification agents, ophthalmological osmotic dehydrating agents, otic preparations, oxytocics, parashypatholytics, parathyroid preparations, pediculicides, phosphorus preparations, premenstrual therapeutics, psychostimulants, quinidines, radiopharmaceuticals, respiratory stimulants, salt substitutes, scabicides, sclerosing agents, sedatives, sympatholytics, sympathomimetics, thrombolytics, thyroid preparations, tranquilizers, tuberculosis preparations, uricosuric agents, urinary acidifiers, urinary alkalinizing agents, urinary tract analgesic, urological irrigants, uterine contractants, vaginal therapeutics and vitamins and each specific compound or composition listed under each of the foregoing categories in the *Physicians' Desk Reference*, (supra).

The polymers of the present invention are used in an amount sufficient to form a matrix around the composition or material to be released in the time release formulations or to act as a carrier for such compositions or materials in such formulations and can be employed in an amount sufficient to permit the delayed time release of a composition or material into its environment, e.g., anywhere from about 1% by weight to about 99% by weight of the time release formulation and preferably from about 5% by weight to about 99% by weight of the time release formulation.

The invention now will be described with respect to the following examples; it is to be understood, however, that the scope of the present invention is not intended to be limited thereby.

EXAMPLE 1

Synthesis of Polyphosphazene Copolymers Containing Trifluoroethoxy and Carboxylatophenoxy Side Groups Polyphosphazene copolymers containing trifluoroethoxy side groups were synthesized using the procedure below. Polymer compositions, molecular weights, yields, the amount of nucleophilic reaction, and NMR characterization data are shown in Table 1. The quantities of the reagents presented below were used for the synthesis of polymer 2 (Table 1). 1.83 g (10.1 mmol) of propyl paraben was reacted with 0.214 g (8.48 mmol) of sodium hydride (95%) in 10 mL of diglyme. The resulting solution was added slowly to a solution of 1.4 g (12.1 mmol) of poly (dichlorophosphazene) in 25 ml of diglyme at 50° C. The temperature was increased to 90° C., and the reaction mixture was then cooled to ambient temperature and then diluted with 50 mL of tetrahydrofuran (THF). 3.0 g (30 mmol) of 2,2,2-trifluoroethanol was reacted with 0.64 g (25.4 mmol) of sodium hydride (95%) in 10 mL of THF. The resulting solution was added slowly to the reaction mixture containing polyphosphazene. The reaction was continued at room temperature for 24 hours. After the completion of the reaction the tetrahydrofuran was evaporated by heating, the reaction temperature was increased to 90° C. and 15 mL of 12.7 N aqueous potassium hydroxide solution was slowly added. The reaction was continued with stirring for one hour and then the polymer was recoverd by precipitating in 165 mL of 0.4 N aqueous hydrochloric acid. Additionally, the polymer was purified two times by re-dissolving it in 50 mL of tetrahydrofuran and precipitating in 210 mL of 0.2 N aqueous hydrochloric acid. The yield after drying in vacuum was 2.32 g.

The disclosures of all patents and publications, including published patent applications, are hereby incorporated by reference to the same extent that each patent and publication were individually incorporated by reference.

It is to be understood, however, that the scope of the present invention is not to be limited to the specific embodiments described above. The invention may be practiced other than as particularly described and still be within the scope of the accompanying claims.

What is claimed is:

1. A polyphosphazene polymer having the formula:

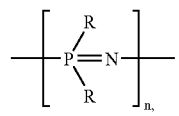

wherein, in each monomeric unit of said polymer, each R is the same or different, and wherein at least a portion of the R groups are $R_1$ groups, and at least a portion of the R groups are $R_2$ groups,
wherein $R_1$ has the formula:

—$Y_1$-$X_1$-$Z_1$, wherein $Y_1$ is oxygen, nitrogen, or sulfur, $X_1$ is selected from the group consisting of alkyl, aryl, aralkyl, alkylaryl, allyl, alkoxy, aryloxy, alkylarloxy, alkylamino, arylamino, and alkylarylamino, and $Z_1$ is an anionic moiety selected from the group consisting of carboxylic acid moieties, sulfonic acid moieties, phosphonic acid moieties, or salts thereof;
$R_2$ has the formula:

—$Y_2$-$X_2$-$Z_2$, wherein $Y_2$ is oxygen, nitrogen, or sulfur, $X_2$ is selected from the group consisting of alkyl, aryl, aralkyl, alkylaryl, allyl, alkoxy, aryloxy, alkylaryloxy, alkylamino, arylamino, and alkylarylamino, and $Z_2$ is a fluorine-containing moiety; and
n is from about 10 to about 300,000.

2. The polymer of claim 1 wherein n is from about 5,000 to about 20,000.

3. The polymer of claim 1 wherein each of $Y_1$ and $Y_2$ is oxygen.

TABLE 1

Polyphosphazene copolymers containing carboxylatophenoxy and trifluoroethoxy side groups.

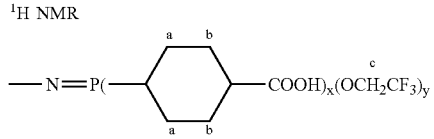

| Polymer | Propyl Paraben, % of PDCP | Polymer Composition: —OPhCOO⁻, % | Yield % | $M_w$, g/mole | $^1$H NMR |
|---|---|---|---|---|---|
| 1 | 15 | 3.0 | 52.3 | 180,000 | 6.9–7.4 (a); 7.8–8.0 (b) 4.2–4.9 (c) |
| 2 | 35 | 14.3 | 71.6 | 295,000 | 6.7–7.3 (a); 7.5–7.9 (b); 4.1–4.6 (c) |
| 3 | 50 | 38.6 | 51.4 | 246,000 | 6.6–7.3 (a); 7.5–7.9 (b); 3.8–4.6 (c) |

4. The polymer of claim 1 wherein the ratio of $R_1$ to $R_2$ in said polymer is from 1:99 to 99:1.

5. The polymer of claim 1 wherein $Z_2$ is $CF_3$ or $CF_2H$.

6. The polymer of claim 1 wherein at least a portion of said R groups are $R_3$ side groups, wherein said $R_3$ side groups are selected from the group consisting of side groups suitable for cross-linking said polymer, side groups to improve the mechanical properties of said polymer, biodegradable side groups, and side groups to improve water solubility and hydrophilicity of said polymer.

7. The polymer of claim 6 wherein said $R_3$ side group is a side group suitable for cross-linking said polymer.

8. The polymer of claim 7 wherein said side group suitable fro cross-linking said polymer is selected from the group consisting of eugenoxy groups, allyloxy groups, alkylphenoxy groups, chlorophenoxy goups, and chlorine.

9. The polymer of claim 6 wherein said $R_3$ side group is a side group to improve the mechanical properties of said polymer.

10. The polymer of claim 9 wherein said side groups to improve the mechanical properties of said polymer is selected from the group consisting of alkylphenoxy groups and phenylphenoxy groups.

11. The polymer of claim 6 wherein said $R_3$ side group is a side group is a biodegradable side group.

12. The polymer of claim 11 wherein said biodegradable side group is selected from the group consisting of chlorine, amino acids, amino acid esters, imidazolyl groups, glycinyl groups, glyceryl groups, glycosyl groups, and ethoxy groups.

13. The polymer of claim 6 wherein said $R_3$ side group is a side group that improves the water solubility and hydrophilicity of said polymer.

14. The polymer of claim 13 wherein said side group that improves the water solubility and hydrophilicity of said polymer is an alkylether side group.

15. A composition comprising a pharmaceutical and a matrix of the polymer of claim 1.

16. A fuel cell membrane comprising the polymer of claim 1.

17. A dopant for an electrically conductive polymer comprising the polymer of claim 1.

18. A multilayer coating for a biomedical device comprising the polymer of claim 1.

19. A in situ cross-linkable material for an injectable implant comprising the polymer of claim 1.

* * * * *